US005697784A

United States Patent [19]
Häfele et al.

[11] Patent Number: 5,697,784
[45] Date of Patent: Dec. 16, 1997

[54] DENTAL CLEANING DEVICE WITH A GRIP MEMBER

[75] Inventors: Peter Häfele, Unterbergen; Ernst Poganitsch, Klagenfurt, both of Austria

[73] Assignee: U.S. Philips Corporation, New York, N.Y.

[21] Appl. No.: 492,829

[22] Filed: Jun. 20, 1995

[30]  Foreign Application Priority Data

Jun. 22, 1994 [AT] Austria .................. 1232/94

[51] Int. Cl.$^6$ .................................................. A61C 1/10
[52] U.S. Cl. .................... 433/85; 433/80; 433/100; 601/162
[58] Field of Search .................... 433/80, 84, 85, 433/88, 98, 99, 100; 601/162, 165

[56]  References Cited

U.S. PATENT DOCUMENTS

| | | | |
|---|---|---|---|
| 4,363,626 | 12/1982 | Schmidt et al. | 433/85 |
| 4,655,198 | 4/1987 | Hommann | 433/80 |
| 5,344,317 | 9/1994 | Pacher et al. | 433/85 |

FOREIGN PATENT DOCUMENTS

3012285  10/1981  Germany.

Primary Examiner—Cary E. O'Connor
Attorney, Agent, or Firm—Ernestine C. Bartlett

[57] ABSTRACT

A dental cleaning device (1) is provided with a mouthpiece (6) and with a grip member (4) having a fluid channel (83, 76, 75, 67, 69, 70, 71, 93, 94) and having a fluid-flow control device (61) which is adjustable an actuating member (8), which is movable between different actuating positions to change the amount of fluid supplied to the mouthpiece (6) through the fluid channel (83, 76, 75, 67, 69, 70, 71, 93, 94), the grip member (4) is provided with activatable parts (83, 76, 75, 67, 72, 73, 74, 32, 94) for temporarily increasing the amount of fluid supplied to the mouthpiece (6) while the instantaneous actuating position of the actuating member (8) for the fluid-flow control device (61) is maintained.

14 Claims, 8 Drawing Sheets

DENTAL CLEANING DEVICE WITH A GRIP MEMBER

FIELD OF THE INVENTION

The invention relates to a dental cleaning device comprising a mouthpiece and a grip member having a fluid channel for supplying fluid to the mouthpiece and having a fluid-flow control device which is adjustable by means of an actuating member, which is movable between different actuating positions, and by means of which the amount of fluid supplied to the mouthpiece through the fluid channel is variable in accordance with the actuating positions of the actuating member.

BACKGROUND OF THE INVENTION

A dental cleaning device of the type defined in the opening paragraph is known, for example from DE-A1-30 12 285. The known dental cleaning device is a dental-jet device whose grip member comprises a control means in the form of an adjustment wheel. The adjustment wheel is connected to a rotatable valve body of a valve provided as fluid-flow control means. An amount of fluid which flows through the fluid channel in a given time interval, which fluid is supplied to the mouthpiece of the dental-jet device and is adequate for a normal cleaning operation, is adjustable by turning the valve body by means of the adjustment wheel in order to supply this amount of fluid. The amount of fluid is below a maximum possible flow and is selected by the user, is supplied to the mouthpiece of the dental-jet device. In order to increase the fluid supply to the mouthpiece after the fluid flow has been adjusted by means of the adjustment wheel, for example in order to remove very persistent residual food particles, the adjustment wheel on the grip member of the known dental-jet device should be rotated from a previously selected setting for a desired fluid flow to a setting for an increased fluid flow. As a result the previously selected setting of the adjustment wheel for the previously desired fluid flow adequate for a normal cleaning operation is lost. Moreover, in the known dental-jet device the fluid flow supplied to a mouthpiece cannot be increased beyond the maximum fluid flow dictated by the dimensioning of the fluid channel and the fluid-flow control means.

SUMMARY OF THE INVENTION

An object of the invention is to mitigate the above problems and to provide a simple way of obtaining a simple and rapid supply of an increased amount of fluid to a mouthpiece via the grip member of a dental cleaning device of the type defined in the opening paragraph, without the setting of the control for the fluid-flow control means having to be altered.

To this end, according to the invention, a dental cleaning device of the type defined in the opening paragraph is characterized in that the grip member is provided with activatable means for temporarily increasing the amount of fluid supplied to the mouthpiece while the instantaneous actuating position e.g., the setting of the actuating member for the fluid-flow control device at the time of activation of the activatable means, is preserved. Thus, it is achieved in a simple manner that by activating the means provided for this purpose on the grip member of the dental cleaning device an increased amount of fluid can be supplied very rapidly and simply to the mouthpiece connected to this grip member without the setting of the control for the fluid-flow control means having to be changed for this, so that this setting is maintained when the fluid flow is increased for an intensified cleaning action and, consequently, the fluid flow selected before this increase and adequate for a normal cleaning action is available immediately after the increased fluid supply has ceased.

In a dental cleaning device in accordance with the invention it has proved to be very advantageous if the activatable means comprise an additional fluid channel and a closing means which is switchable between a closed state and an open state to close and open the additional fluid channel. Thus, an increased fluid flow, which is independent of the dimensioning of the fluid channel of the fluid-flow control means, can be applied to the mouthpiece of a dental cleaning device in accordance with the invention in a very simple manner.

It has further proved to be very advantageous if the grip member carries an actuating member which is operable by hand and movable from a rest position into an operating position in order to actuate the closing means, and the closing means occupies its open position and opens the additional fluid channel when the actuating member is in its operating position. This results in a very simple construction, which for an increased fluid flow merely requires the actuation of the actuating member provided on the grip member which is held in one hand during operation, in order to set it from its rest position to its operating position with this hand. The advantage is that this is possible without changing the position of the hand.

In an advantageous embodiment of a dental cleaning device in accordance with the invention the closing means is formed by a conical valve having an axially movable valve body which is loaded by a pressure spring, which urges the valve body in a direction from an open position corresponding to the open state of the closing means towards a closed position corresponding to the closed state of the closing means. This provides a self-closing closing means, which guarantees that the additional fluid channel is shut off when the actuating member is set to its rest position.

Another preferred embodiment of a dental cleaning device in accordance with the invention is characterized in that the actuating member is arranged on a slide which is guided so as to be movable in the longitudinal direction of the grip member and which is slidable between an off-position and an on-position, and in that with the slide in its off-position the closing means cannot be switched over by the actuating member and with the slide in its on-position the closing means can be switched over from its closed state to its open state by the actuating member. This ensures that the actuating member provided on the slide can be set to a position on the grip member in which the closing means cannot be changed over, so that an increased fluid flow to the mouthpiece connected to the grip member can be stopped deliberately.

In such an embodiment of a dental cleaning device in accordance with the invention it has proved to be advantageous if the actuating member includes a push-button subjected to the load of a pressure spring, which acts upon the slide and which urges the push-button in a direction from the operating position towards the rest position of the actuating member. This results in a very simple and reliable construction.

In a dental cleaning device in accordance with the invention having a slide which is guided so as to be movable in the longitudinal direction of the grip member of the dental cleaning device, it has also proved to be very advantageous if the slide comprises an actuating portion and the fluid channel includes a further closing means which is movable between a closed state and an open state to close and open the fluid channel, which further closing means is switchable by means of the actuating portion of the slide, and the further closing means is in its closed state when the slide is in its off-position and the further closing means is in its open state when the slide is in its on-position. This ensures that in the off-position of the slide both the fluid channel and the additional fluid channel are shut off and that the additional fluid channel can be opened only when the fluid channel is open, in order to boost the fluid flow to the mouthpiece connected to the grip member.

In such an embodiment of a dental cleaning device in accordance with the invention it has proved to be very advantageous if the further closing means is formed by a further conical valve having an axially movable valve body which is loaded by a pressure spring, which urges the valve body in a direction from an open position corresponding to the open state of the further closing means towards a closed position corresponding to the closed state of the further closing means. This results in a further self-closing closing means, which guarantees that the fluid channel is shut off when the slide is moved to its off-position.

It has proved to be particularly advantageous if the push-button is included in a slide knob which is guided so as to be movable in the longitudinal direction of the grip member and which traverses the slide knob with its part which points away from the grip member. This enables both the push-button and the slide knob to be actuated with the thumb of the hand in which the grip member is held.

BRIEF DESCRIPTION OF THE DRAWINGS

The invention will now be described in more detail with reference to the drawings, which show an exemplary embodiment to which the invention is not limited.

DETAILED DESCRIPTION OF THE PREFERRED EMBODIMENTS

Figure 1:
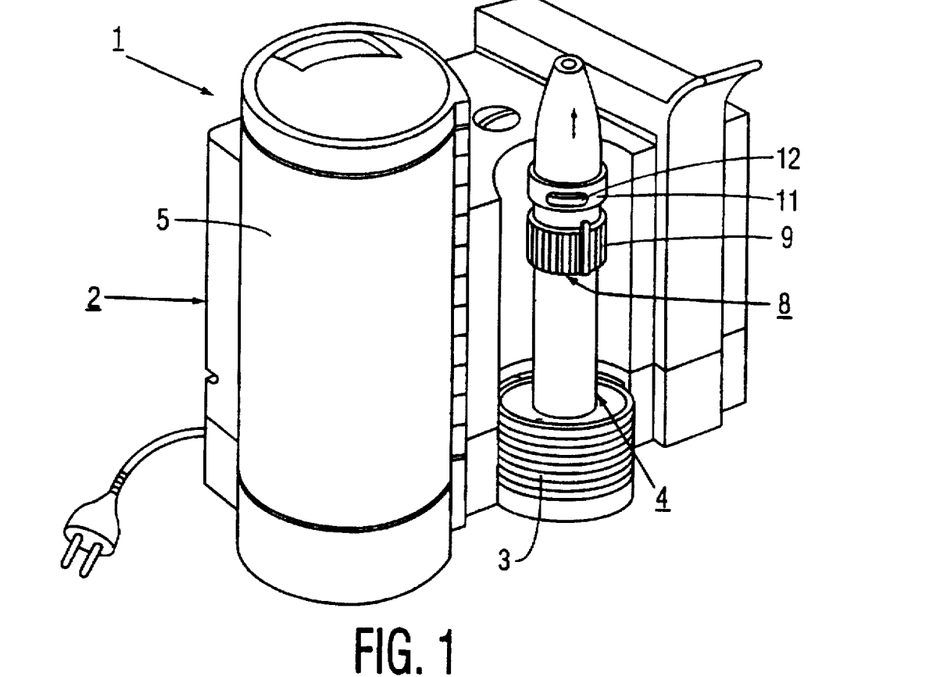
FIG. 1 is a diagrammatic oblique view of a dental-jet device, comprising a basic appliance and a grip member which is connected to the basic appliance via a tube and which can be fitted with different mouthpieces.

FIG. 1 shows a dental cleaning device constructed as a dental-jet device 1, which comprises a basic appliance 2 and a grip member 4 connected to the basic appliance 2 via a flexible tube 3. A fluid container 5 is placed on the basic appliance 2, which comprises a motor-driven pump means by which a fluid, for example water, can be pumped from the fluid container 5 to the grip member 4 via the tube 3. The grip member 4 can be provided with different mouthpieces, as is shown for a mouthpiece 6 in FIG. 2. The fluid pumped to the grip member 4 is fed to the mouthpiece 6 to form a jet via a nozzle 7 of the mouthpiece 6 in order to clean the teeth and the gums and to massage the gums.

In order to select a desired fluid flow to the mouthpiece 6 the grip member 4 has an adjustable actuating member 8 for a fluid-flow control means. The actuating member 8 comprises an adjustment ring 9 which is flexible in the direction of the grip member 4. The construction of the actuating member 8 will be described in more detail hereinafter. By turning the adjustment ring 9 the fluid-flow control means in the grip member 4 can be set to the desired fluid flow to be supplied to mouthpiece 6. The construction of the fluid-flow control means will be described in greater detail hereinafter.

Figure 2:
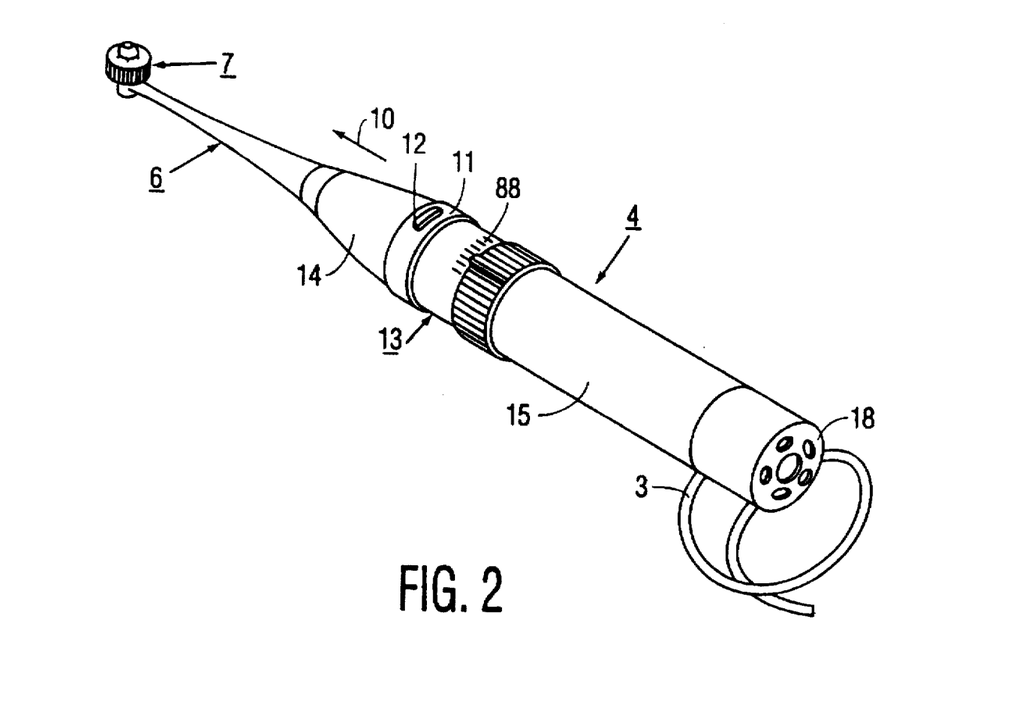
FIG. 2 is a diagrammatic oblique view of the grip member of the dental-jet device shown in FIG. 1, a mouthpiece being fitted onto the grip member, which mouthpiece has a nozzle at its free end.
Figure 3:
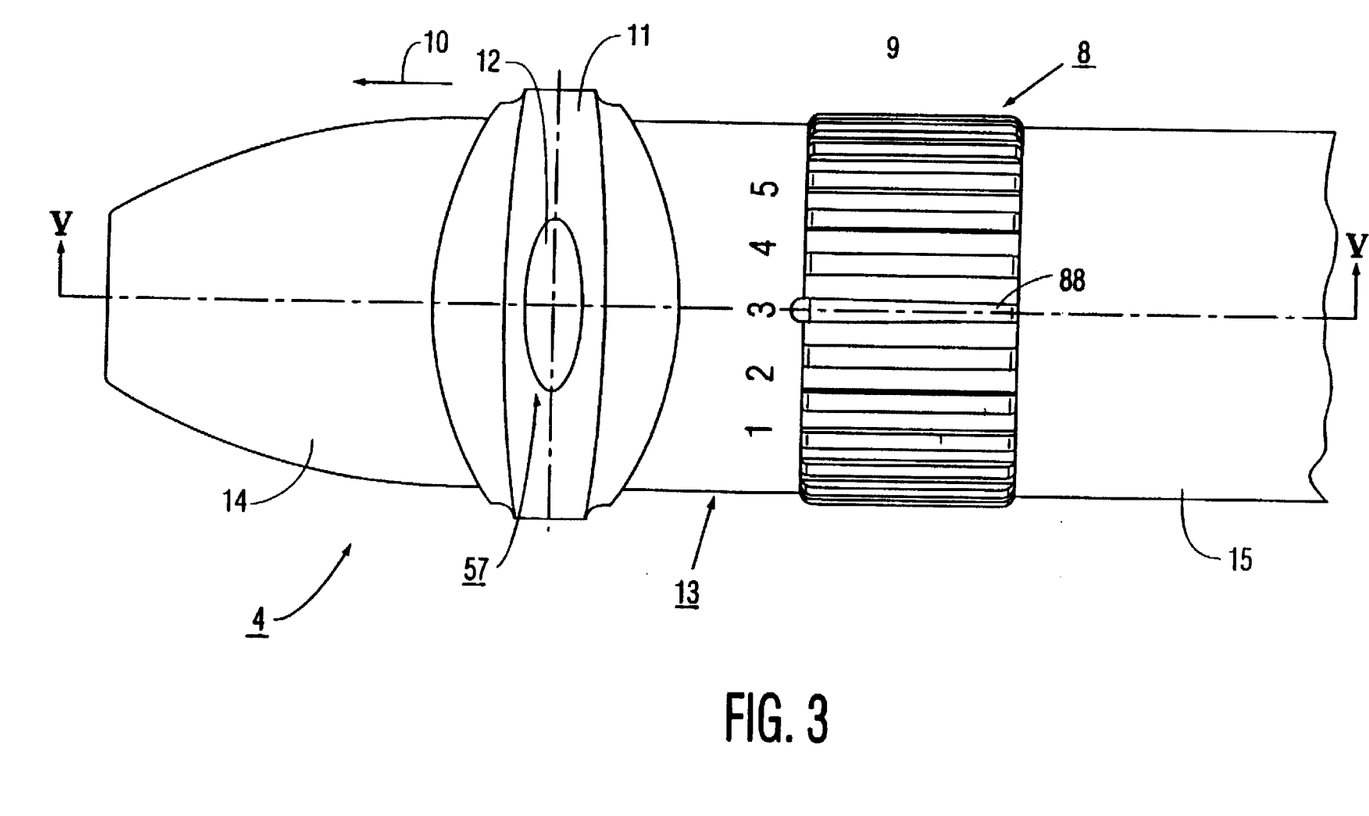
FIG. 3 is a plan view of a relevant part of the mouthpiece shown diagrammatically in FIGS. 1 and 2.

The grip member 4 further comprises a slide knob 11 which is guided so as to be movable in the longitudinal direction of the grip member 4 indicated by the arrow 10 and in a direction opposite thereto, between an off-position shown in FIG. 2 and an on-position shown in FIGS. 3 to 8. When the slide knob 11 is in the on-position shown in FIGS. 3 to 8 the water supply from the tube 3 to the mouthpiece 6 via the grip member 4 is interrupted and when the slide knob 11 is in its on-position water supply from the tube 3 to the mouthpiece 6 via the grip member 4 is possible.

A push-button 12 included in the slide knob 11 has a part which points away from the grip member 4 and traverses the slide knob 11. The function of the push-button 12 will be described in detail hereinafter.

The grip member 4 of the dental-jet device 1 has an elongate sleeve-shaped plastic housing 13 comprising a first housing section 14, situated nearest a mouthpiece 6, and a second housing section 15, whose end adjoins the end of the first housing section 14 at the location of the flexible adjustment ring 9. At its free end the first housing section 14 has an opening 16 through which the interior of an inner tubular housing portion 17 is accessible. A mouthpiece 6 can be inserted into the tubular housing portion 17 through the opening 16 to couple this mouthpiece 6 to the grip member 4 in a fluid-transmitting manner. At its free end the second housing section 15 has a bottom 18, as is shown in FIG. 2.

The tubular portion 17 of the first housing section 14 is adjoined by a plastic tubular coupling member 19 located in the first housing section 14 and having a comparatively thick-walled portion 20 into which the end of a mouthpiece 6 can be introduced. At the location of the comparatively thick-walled portion 20 a wire spring 21 is arranged having a circular shape over an angle of substantially 270° and having straight end portions 21a and 21b which extend substantially parallel to one another and towards the interior of the circular spring. The two spring ends 21a and 21b can hold a mouthpiece 6 onto the grip member 4 in that the spring ends 21a and 21b engage a groove provided for this purpose in the mouthpiece 6. The end of a mouthpiece 6 held by means of the spring 21 then lies against a sealing ring 22 fitted in the comparatively thick-walled portion 20 of the coupling member 19.

Figure 4:
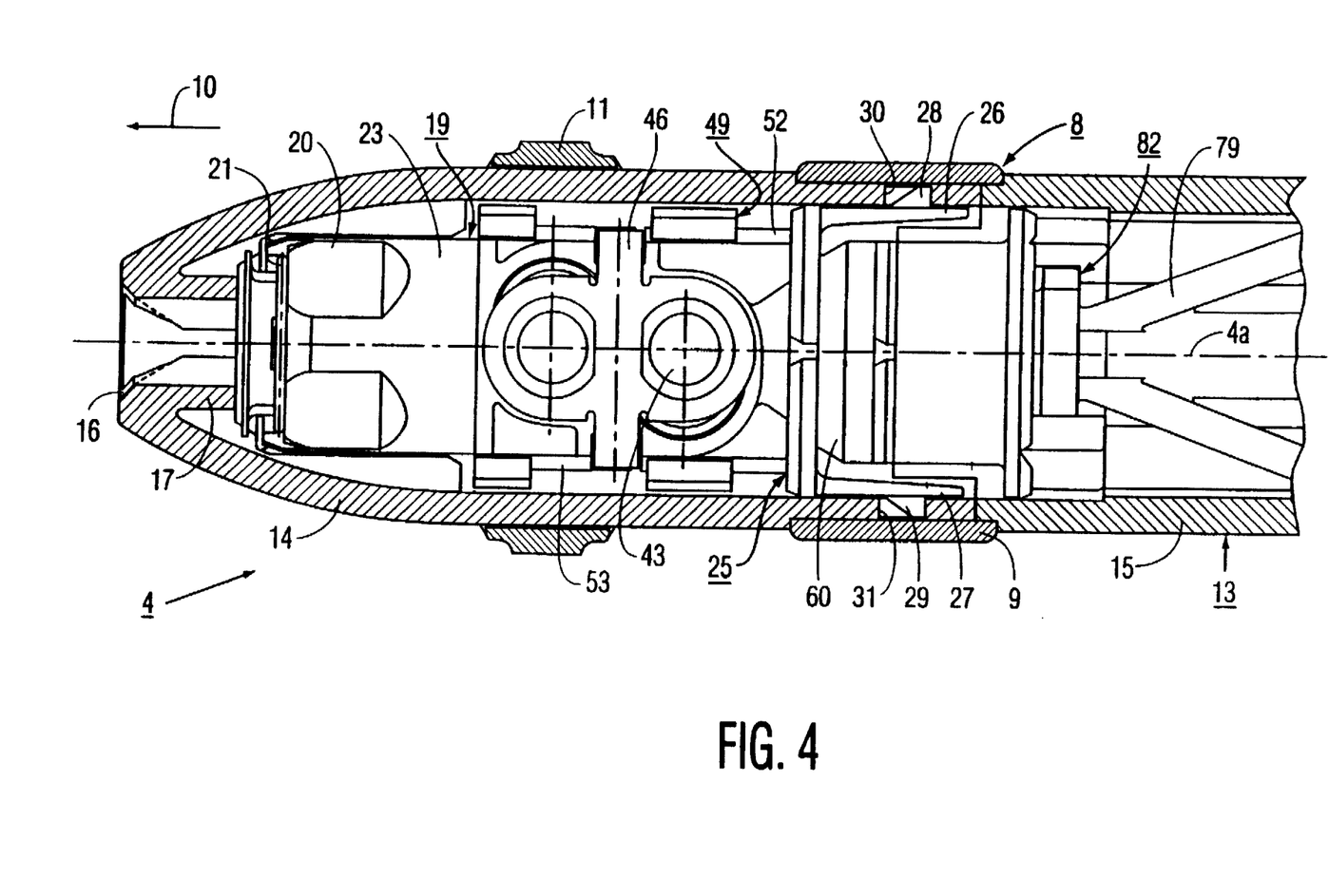
FIG. 4 is an underneath view of the part of the mouthpiece shown in FIG. 3 with the housing partly cut away, the sectional view of the housing being taken parallel to the plane of drawing in FIG. 3 and through the axis of the grip member.
Figure 5:
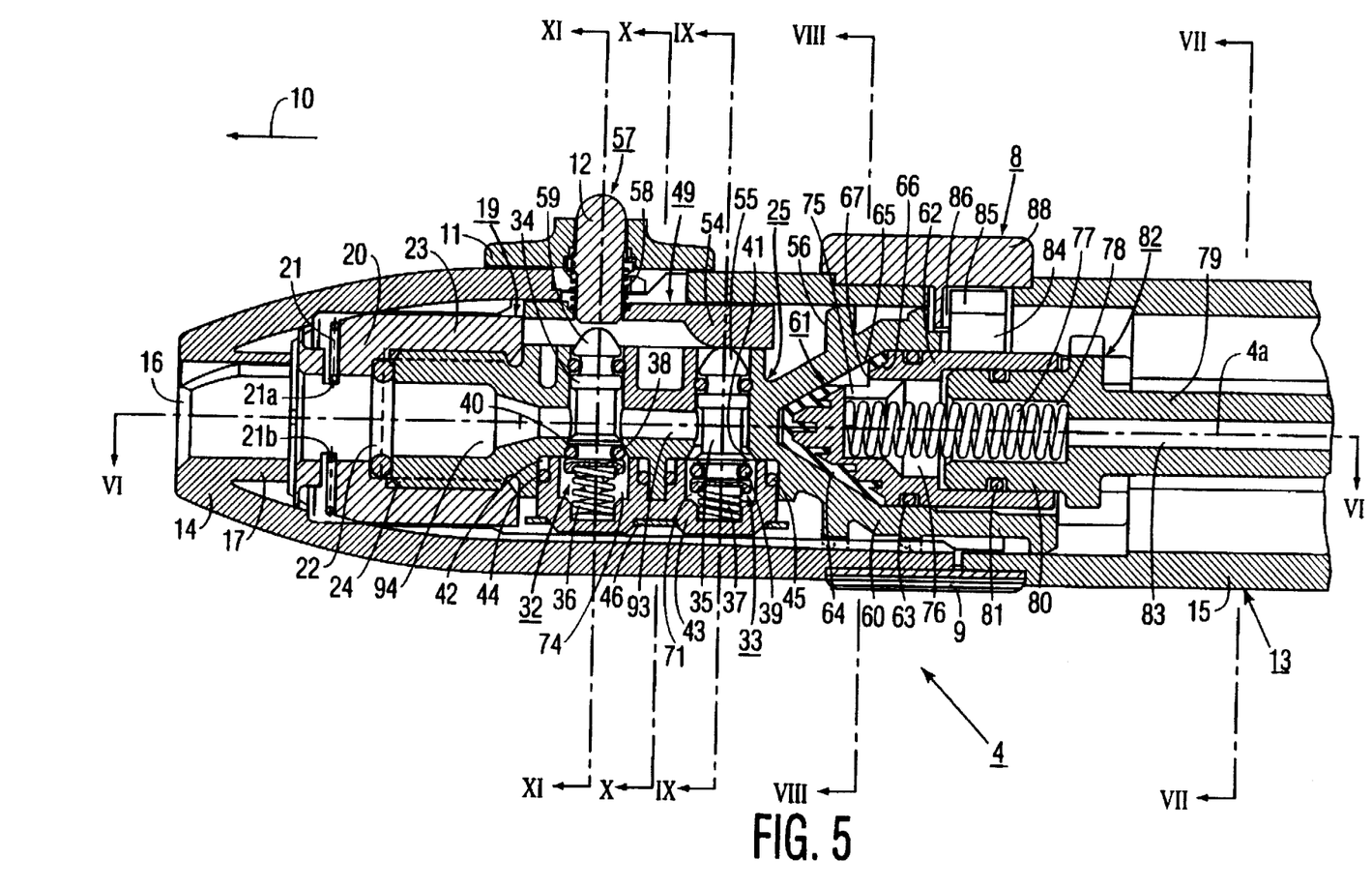
FIG. 5 shows the part of the grip member shown in FIGS. 3 and 4 in a sectional view taken on the line V—V in FIG. 3.
Figure 6:
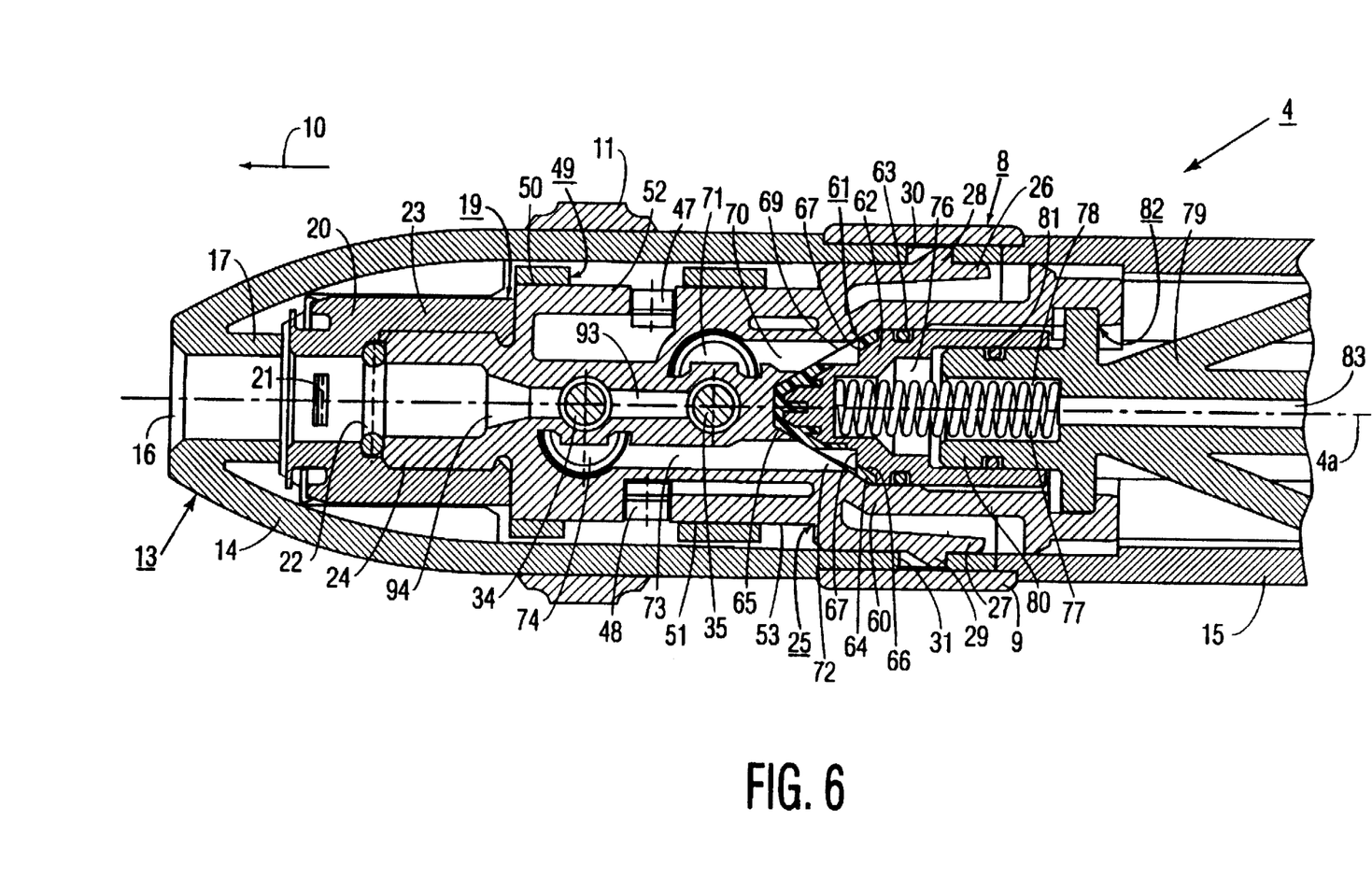
FIG. 6 shows the part of the grip member shown in FIGS. 3, 4 and 5 in a sectional view taken on the line VI—VI in FIG. 5.
Figure 7:
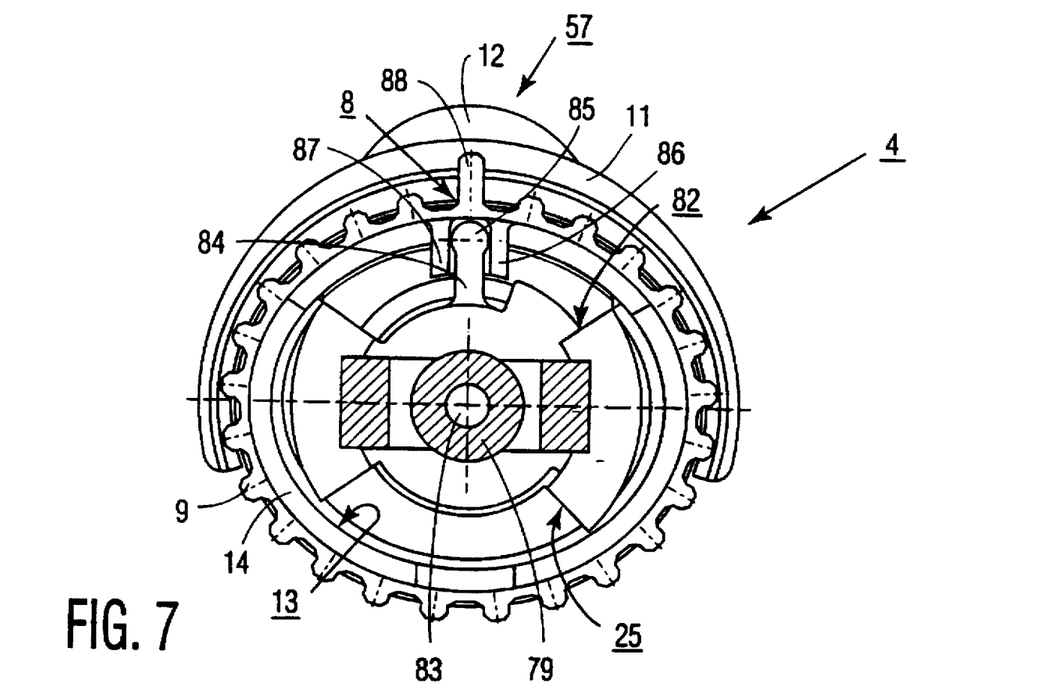
FIG. 7 shows a detail of the part of the grip member shown in FIGS. 3, 4, 5 and 6 in a sectional view taken on the line VII—VII in FIG. 5.

The coupling member 19 is connected to a plastic valve housing 25 by a comparatively thin-walled portion 23 by screwthread means 24, shown diagrammatically in FIGS. 5 and 6. As is apparent from FIGS. 4 and 6 the valve housing 25 is retained in the first housing section 14 by means of two resilient latching arms 26 and 27, which project laterally from the valve housing 25, two latching noses 28 and 29 provided on the latching arms 26 and 27 engaging into two latching recesses 30 and 31 formed in the first housing section 14 after the valve housing 25 with the coupling member 19 secured thereto has been inserted into the first housing section 14. The latching recesses 30 and 31 and the latching noses 28 and 29 are covered by the flexible adjustment ring 39.

As is apparent in particular from FIG. 5, the valve housing 25 accommodates a first closing means 32 and a second closing means 33. Both closing means 32 and 33 are switchable between a closed state and an open state. In FIG. 5 the first closing means 32 is shown in its closed state and the second closing means 33 in its open state. The closing means 32 and 33 each comprise a conical valve having a valve body, 34 and 35, which is movable in the axial direction of the conical valve. Each of the two valve bodies 34 and 35 is loaded by a pressure spring 36 and 37, respectively, which urges the relevant valve body 34 or 35 from an open position corresponding to the open state of the respective closing means 32 or 33 to a closed position corresponding to the closed state of the respective closing means 32 or 33. Each of the two valve bodies 34 and 35 is provided with two sealing rings to ensure a correct sealing. Of these sealing rings two sealing rings 38 and 39 cooperate with conical valve surfaces 40 and 41 of the valve housing 25 in the closed positions of the relevant valve bodies 34 and 35. The two closing means 32 and 33 guarantee a particularly reliable and self-closing operation.

For the insertion of the valve bodies 34 and 35 and the pressure springs 36 and 37 into the valve housing 25 the valve housing 25 has an opening 42 in its bottom area, which opening is closed by means of a valve-housing cover 43 with two interposed seals 44 and 45. To secure the valve-housing cover 43 to the valve housing 25 there is provided a clip 46 of substantially omega-shaped cross-section made of a resilient sheet material; whose bent end portions 47 and 48 engage with the valve housing 25, as is apparent in particular from FIG. 10.

A switching slide 49 is guided on the valve housing 25 so as to be movable in a direction indicated by the arrow 10 and in the opposite direction. The switching slide 49 has a substantially arcuate cross-sectional shape, as is apparent from FIGS. 7 to 11. The two lateral end portions of the switching slide 49 are divided into two parts in the longitudinal direction of the grip member 4, the two parts forming between them a recess for the clamping arms of the resilient clip 46, as is shown in FIGS. 4 and 6. To guide the switching slide 49 on the valve housing 25 the switching slide 49 has discontinuous guide slots 50 and 51 in its two lateral end portions, which slots are each engaged by a laterally projecting guide rib 52 and 53, respectively, as is apparent from FIGS. 4, 6 and 9 to 11. The switching slide 49 is slidable between an on-position shown in FIGS. 3 to 11 and an off-position not shown in the Figures.

Figure 9:
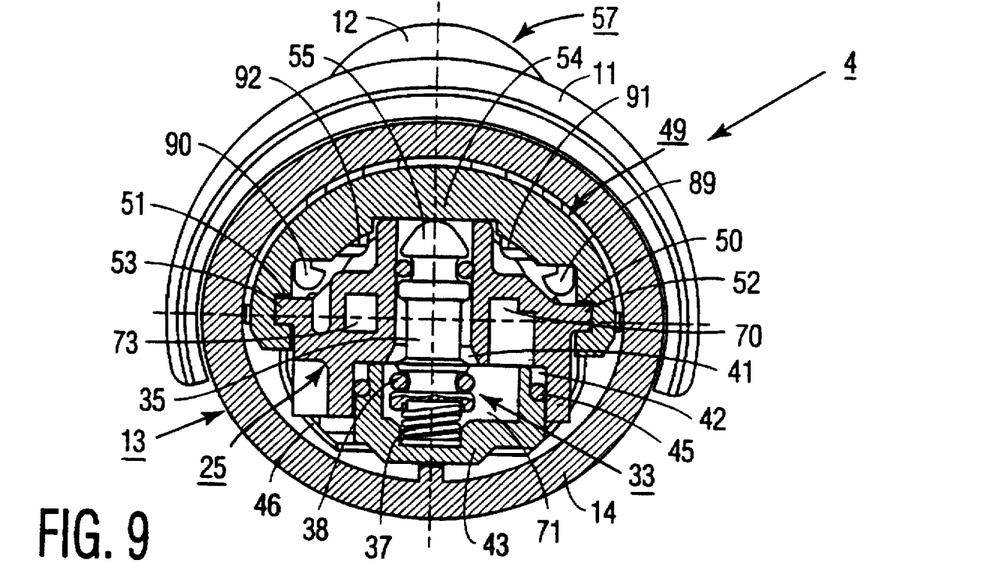
FIG. 9 shows a detail of the part of the grip member shown in FIGS. 3, 4, 5 and 6 in a sectional view taken on the line IX—IX in FIG. 5.

As is apparent from FIGS. 5 and 9 the switching slide 49 has an actuating portion 54. The second closing means 33 can be switched over by means of this actuating portion 54 of the switching slide 49, namely in that the actuating portion 54 cooperates with a head portion 55 of the valve body 35 of the conical valve forming the second closing means 33. FIGS. 5 and 9 show the switching slide 49 is in its on-position, the second closing means 33 then being in its open state in which its valve body 35 is in the open position. From the on-position shown in FIGS. 5 and 9 the switching slide 49 is movable into an off-position in a direction opposite to that indicated by the arrow 10, in which off-position the actuating portion 54 of the switching slide 49 abuts against a stop 56 which projects from the valve housing 25. When the switching slide 49 is in its off-position the second closing means 33 will be in its closed state because the pressure spring 37 of the second closing means 33 then keeps valve body 35 in its closed position, the sealing ring 39 then lying on the conical valve surface 41 of the valve housing 25.

To switch the first closing means 32 between its closed state and its open state the grip member 4 carries an actuating member 57 which is operable by hand. Suitably, the actuating member 57 is arranged on the switching slide 49. The actuating member 57 comprises the push-button 12 and a pressure spring 58 which acts upon the push-button 12 and on the switching slide 49. The actuating member 57 is movable between a rest position shown in FIGS. 1, 2, 3, 5, 7, 8, 9, 10 and 11 and an operating position not shown in the Figures, into which it can be set by depressing the push-button 12. As long as the actuating member 57 occupies its rest position, the first closing means 32 will be in its closed state, as is apparent from FIG. 5. Once the actuating member 57 has been set into its operating position by depression of the push-button 12, the first closing means 32 will be in its open state.

Suitably, the actuating member 57 is arranged on the switching slide 49, which is guided so as to be movable in the longitudinal direction of the grip member 4 between its on-position shown in FIG. 5 and its off-position not shown in FIG. 5. Thus, as is apparent from FIG. 5, it is simply achieved that with the switching slide 49 in the on-position the first closing means 32 can be switched from its closed state to its open state by means of the actuating member 57, and that with the switching slide 49 in its off-position the first closing means 32 cannot be changed over by means of the actuating member 57. With the switching slide 49 in its on-position the first closing means 32 is changed over by means of the actuating member 57 in that, opposed by the force of the pressure spring 58, the push-button 12 is pressed by hand against a head portion 59 of the valve body 34 of the first closing means 32, the valve body 34 then being moved into its open position against the force of the pressure spring 36 and the sealing ring 38 being lifted off the conical valve surface 40 of the valve housing 25.

Adjacent its area with the two closing means 32 and 33 the valve housing 25 has a substantially funnel-shaped portion 60 which forms a part of a fluid-flow control means 61. In addition to the funnel-shaped portion 60 the fluid-flow control means 61 comprises a substantially conical plastic valve body 62, which is fitted in the funnel-shaped portion 60 with an interposed sealing ring 63 and in the present grip member 4 is rotatable relative to the funnel-shaped portion 60 of the valve housing 25 about the longitudinal axis 4a of the grip member 4.

Figure 8:
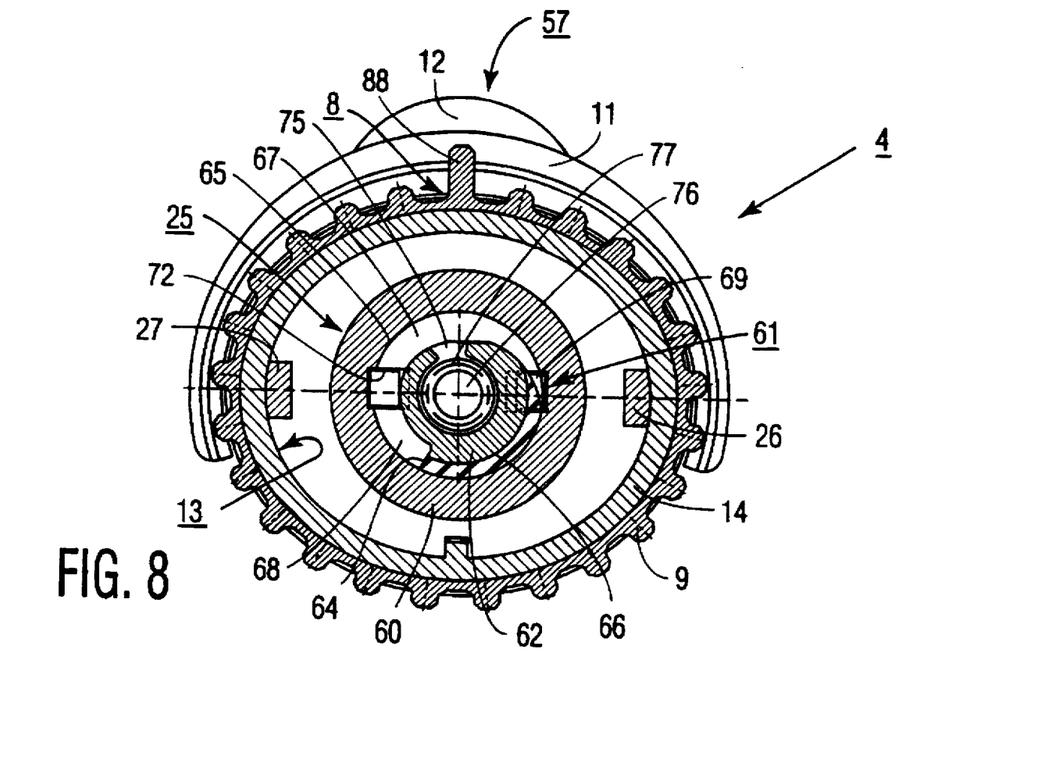
FIG. 8 shows a detail of the part of the grip member shown in FIGS. 3, 4, 5 and 6 in a sectional view taken on the line VIII—VIII in FIG. 5.

At the location of its substantially conical portion the valve body 62 has a rubber sealing cap 64 which lies against the inner conical bounding surface 65 of the funnel-shaped portion 60 of the valve housing 25. At the location of its outer conical bounding surface 66 the valve body 62 has a circumferential recess 67 which is not covered by the sealing cap 64 and which, as is apparent from FIGS. 5 and 6, has a triangular cross-sectional shape in a longitudinal sectional view of the grip member 4 and a substantially crescent-like cross-sectional shape in a cross-sectional view of the grip member 4, as is apparent from FIG. 8. As is shown in FIG. 8, the recess 67 has the same width from its end 68 over an angular range of approximately 150°, after which the width of this recess 67 decreases continuously towards the other end 68. It is to be noted that this other end of the recess 67 is not visible in FIG. 8 because the other end is situated behind the relevant part of the sealing cap 64 as a result of the fact that the sectional view in FIG. 8 has been taken on the line VIII—VIII in FIG. 5. In its narrowing part the recess 67 in the valve body 62 is situated opposite a first inlet opening 69 in the funnel-shaped portion 60 of the valve housing 25, which as is shown in FIG. 6 is connected to a space 71 via a first intermediate channel 70 formed in the valve housing 25, which space 71 accommodates the pressure spring 37 and is closed by the valve-housing cover 43, as is illustrated in FIGS. 5, 6 and 9. In its part of constant width the recess 67 in the valve body 62 is situated opposite a second inlet opening 72 in the funnel-shaped portion 60 of the valve housing 25. The second inlet opening 72 is connected to a further space 74 via a second intermediate channel 73, which further space 74 accommodates the pressure spring 36 and is closed by the valve-housing cover 43, as is illustrated in FIGS. 5, 6, 9, 10 and 11. By rotating the valve body 62 relative to the funnel-shaped portion 60 of the valve housing 25 the narrowing part of the recess 67 in the valve body 62 is rotated relative to the first inlet opening 69 in the funnel-shaped portion 60, thereby enabling different cross-sectional passages to be obtained. In this way it is possible to obtain fluid-flow control by the rotation of the valve body 62 and the resulting change in cross-sectional passage between the recess 67 and the first inlet opening 69. Owing to the shape of the recess 67 in the valve body 62 in its area opposite the second inlet opening 72, in which area it has a constant width, it is achieved that regardless of the rotary position of the valve body 62 always the same and maximal cross-sectional passage is obtained between the recess 67 and the second inlet opening 72.

The recess 67 in the valve body 62 is connected to an inner space 76 in the valve body 62 via a passage 75 in the valve body 62, as can be seen in FIGS. 5 and 8. The inner space 76 accommodates a pressure spring 77 of which one end acts upon the valve body 62 and thereby presses the valve body 62 with its sealing cap 64 into the funnel-shaped portion 60 of the valve housing 25, and of which the other end acts on a plastics fluid supply member 79 in an inner space 78 of this member 79, which has a hollow cylindrical portion 80 which engages the inner space 76 of the valve body 62 with an interposed sealing ring 81 and which, opposed by the force of the pressure spring 77, is secured to the valve housing 25 by means of a bayonet-type locking device 82. The fluid supply member 79 have a fluid supply channel 83, which is connected to the tube 3 of the dental-jet device 1 in a manner not shown. A screw which extends through the bottom 18 of the second housing section 15 is fitted into the end of the fluid supply member 79 which is not visible in FIGS. 3 to 6, to secure the bottom 18 and hence the second housing section 15 to the fluid supply member 79, which it its turn is connected to the valve housing 25, which is secured in the first housing section 14 by means of the locking device 82.

To rotate the valve body 62 relative to the funnel-shaped portion 60 of the valve housing 25 an arm 84 projects outwardly from the valve body 62, which arm has a cross-sectionally circular end portion 85. The end portion 85 extends between two ribs 86 and 87 which project inwardly from the flexible adjustment ring 9 of the actuating member 8, thereby providing a coupling between the flexible adjustment ring 9 and the valve body 62, as is apparent from FIG. 5 and, particularly, from FIG. 7. For the sake of clarity the second housing section 15 is not shown in FIG. 7. The actuating member 8 can be set from the position shown in FIGS. 3 to 8, in which an indicator ridge 88 on the adjustment ring 9 of the actuating member 8 is situated opposite a scale number "3" on the first housing section 14, to different positions in opposite directions, the valve body 62 being movable in opposite directions through approximately ±45° relative to the position shown in FIGS. 3 to 8 by means of the actuating member 8. The adjustment ring 9 of the actuating member 8 can be adjusted simply with the thumb of the hand in which the grip member 4 is held.

In view of the actuation of the control means on the grip member 4 it has proved to be very advantageous that the push-button 12 of the actuating member 57 is included in the slide knob 11, which is guided so as to be movable in the longitudinal direction of the grip member 4, and traverses the slide knob 11 with its part which is remote from the grip member 4. In this way it is achieved in a simple manner that not only the flexible adjustment ring 9 of the actuating member 8 but also the slide knob 11 as well as the push-button 12 of the actuating member 57 can be actuated simply with the thumb of the hand in which the grip member 4 is held.

Figure 10:
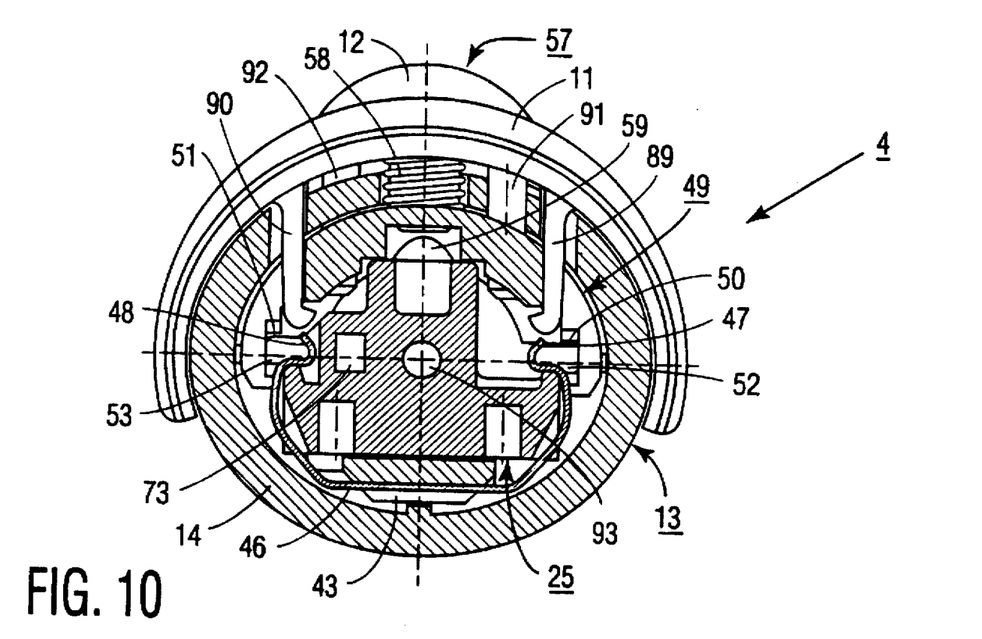
FIG. 10 shows a detail of the part of the grip member shown in FIGS. 3, 4, 5 and 6 in a sectional view taken on the line X—X in FIG. 5.
Figure 11:
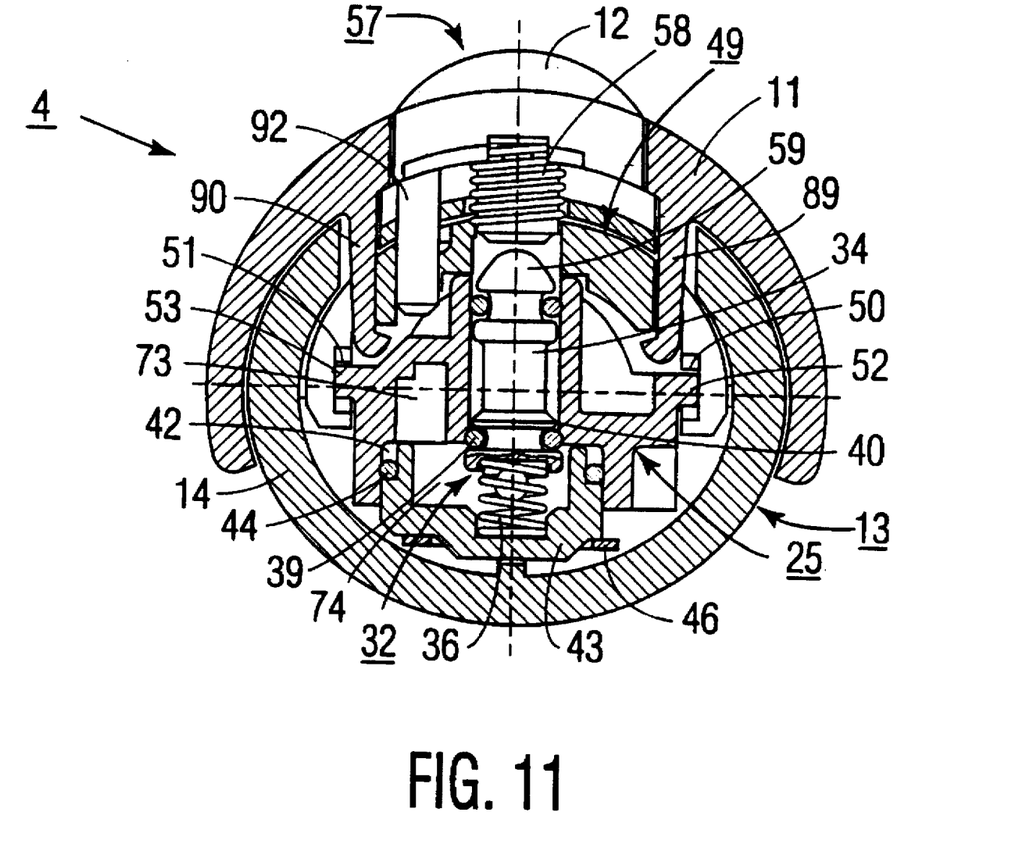
FIG. 11 shows a detail of the part of the grip member shown in FIGS. 3, 4, 5 and 6 in a sectional view taken on the line XI—XI in FIG. 5.

As is apparent from FIGS. 9, 10 and 11 the plastics slide knob 11, after the valve housing 25 together with the coupling member 19, which is secured to the valve housing 25, and the switching slide 49, which is movably guided on the valve housing 25, has been inserted into the first housing section 14, can be fitted onto the first housing section 14, two latching arms 89 and 90, which project from the switching slide 49, and two coupling pins 91 and 92 each being passed through a slot-shaped passage in the first housing section 14. The latching arms 89 and 90 serve to secure the sliding knob 11 to the switching slide 49, and the coupling pins 91 and 92, which are offset from one another in the longitudinal direction of the grip member 4, serve to couple the sliding knob 11 to the switching slide 49, in order to transmit the force exerted by hand on the sliding knob 11 to the switching slide 49. In the same way as the switching slide 49 the sliding knob 11 has a substantially arcuate cross-sectional shape, its two lateral end portions substantially enclosing the first housing section 14, thereby helping to secure the sliding knob 11 to the grip member 4.

In the dental-jet device 1 described with reference to FIGS. 1 to 11 it is assumed in customary manner that the user of the device 1 has set the actuating member 8 to a position, and normally leaves this member in this position, in which the fluid-flow control device 61, which can be adjusted by means of the actuating member 8, has been set to a fluid flow to the mouthpiece 6 connected to the grip member 4, which is convenient and adequate for the user of the dental-jet device 1 in normal operation. Moreover, it is assumed that after use of the present dental-jet device 1 the sliding switch 11 and, consequently, the switching slide 49 coupled thereto via the two coupling pins 91 and 92 have each been set to their off-positions.

When it is now assumed that starting from the initial situation described above a user of the dental-jet device 1 puts this device 1 again into operation the pump means in the basic appliance 2 will be started in that the dental-jet device 1 is switched on, as a result of which fluid is fed from the container 5 to the tube 3 via the pump means and is transferred from this tube to the fluid supply member 79 in the grip member 4. The fluid then reaches the inner space 76 in the valve body 62 via the fluid supply channel 83 in the fluid supply member 79 and from this space it reaches the recess 67 in the valve body 62 via the passage 75 in the valve body 62. From the recess 67 the fluid is fed to the space 71 in the valve body 25, accommodating the pressure spring 37 and closed by the closing means 33 in the closed position, via the first inlet opening 69 in the funnel-shaped portion 60 of the valve housing 25 and the first intermediate channel 70 in the valve housing 25, because the sliding knob 11 and the switching slide 49 are in their off-positions, and in addition the fluid is fed from the recess 67 to the second inlet opening 72 in the funnel-shaped portion 60 of the valve housing 25 and from there, via the second intermediate channel 73 in the valve housing 25, to the space 74 in the valve housing 25, which space accommodates the pressure spring 36 and which is closed by the first closing means 32, which is in its closed state.

For a normal tooth cleaning process the user of the dental-jet device 1 moves the sliding knob 11 in the direction indicated by the arrow 10 from its off-position shown in FIGS. 1 and 2 to its on-position shown in FIGS. 3 to 11. Consequently, the actuating portion 54 of the switching slide 49 sets the second closing means 33 to its open position, as a result of which the sealing ring 39 is lifted off the conical valve surface 41 of the valve housing 25, which surface is adapted to cooperate with this sealing ring 39, so that the space 71 in the valve housing 25 is then in fluid-transmitting communication with a central channel 93 in the valve housing 25. The central channel 93 is then constantly in fluid-transmitting communication with an outlet channel 94 in the valve housing 25, by-passing the valve body 34 of the first closing means 32. From the outlet channel 94 of the valve housing 25 the fluid supplied by the pump means in the dental-jet device 1 is fed to a mouthpiece 6 coupled to the grip member 4, which mouthpiece is locked to the grip member 4 by means of the wire spring 21, the transition between the outlet channel 94 of the valve housing 25 and the mouthpiece 6 being sealed by means of the sealing ring 22.

In the operational situation described above a normal fluid channel in the grip member 4 is open, which channel serves to supply fluid to a mouthpiece 6 in the case of a normal cleaning process. This normal fluid channel includes the fluid supply channel 83 in the fluid supply member 79, the inner space 76 in the valve body 62, the passage 75 in the valve body 62, the recess 67 in the valve body 62, the first inlet opening 69 in the funnel-shaped portion 60 of the valve housing 25, the first intermediate channel 70 in the valve housing 25, the space 71 in the valve housing 25, central channel 93 in the valve housing 25, and finally the outlet channel 94 in the valve housing 25.

The dental-jet device 1 shown in FIGS. 1 to 11 has the advantage that the user of the device can temporarily increase the fluid flow supplied to the mouthpiece 6 in a simple manner while preserving the instantaneous setting of the actuating member 8 for the fluid-flow control device 61, in the case that he or she feels that the fluid flow supplied to the mouthpiece 6 via the normal fluid channel 83, 76, 75, 67, 69, 70, 71, 93, 94 is not adequate. For this the user should merely actuate the push-button 12 while the sliding knob 11 is in its on-position. The first closing means 32 is then set to its open state, as a result of which the sealing ring 38 is lifted off the conical valve surface 40 of the valve housing 25, which surface is adapted to cooperate with this sealing ring 38, so that the space 74 in the valve housing 25, which was previously closed by the sealing ring 38, is then in fluid-transmitting communication with the outlet channel 94. This suddenly opens an additional fluid channel in the grip member 4, via which channel a mouthpiece 6 is supplied with an amount of fluid in addition to the fluid flow fed to the mouthpiece 6 via the normal fluid channel which is opened by the second closing means 33, resulting in an increased fluid flow in the mouthpiece 6. The additional fluid channel includes the fluid supply channel 83 in the fluid supply member 79, the inner space 76 in the valve body 62, the passage 75 in the valve body 62, the recess 67 in the valve body 62, the second inlet opening 72 in the funnel-shaped portion 60 of the valve housing 25, the second intermediate channel 73 in the valve housing 25, the space 74 in the valve housing 25, and finally the outlet channel 94 in the valve housing 25.

As soon as the user of the dental-jet device 1 releases the push-button 12 this button returns to its rest position under the influence of the pressure spring 58, as a result of which the pressure spring 36 also resets the valve body 34, so that the first closing means 32 is in its closed state, in which the additional fluid channel 83, 76, 75, 67, 72, 73, 74, 94 is shut off. Thus, the supply of the additional amount of fluid to a mouthpiece 6 is interrupted immediately after the release of the push-button 12, upon which a mouthpiece 6 again receives the amount of fluid preset by mean of the actuating member 8 via the normal fluid channel 83, 76, 75, 67, 69, 70, 71, 93, 94 because the setting of the actuating device 8 is maintained during the increased fluid supply to a mouthpiece 6. How much additional fluid is supplied to a mouthpiece 67 depends only on the dimensioning of the additional fluid channel 83, 76, 75, 67, 72, 73, 74, 94, the additional amount of fluid not being influenced by the dimensioning of the normal fluid channel 83, 76, 75, 67, 69, 70, 71, 93, 94. The additional fluid channel may also include a fluid-flow control device for controlling the additional fluid flow.

Another variant of the invention may comprise a rotatable conical valve body of a fluid-flow control device provided in the grip member, which valve body is of a construction similar to that in the dental-jet device shown in FIGS. 1 to 11 but is mounted in the grip member not only so as to be rotatable but also to be movable in an axial direction to allow the valve body to be lifted off a funnel-shaped complementary member. In such a variant there is only one outlet opening in the area of the conical surface of the valve body and only one inlet opening in the area of the conical surface of the funnel-shaped complementary member, which openings are tangentially movable relative to one another for the purpose of flow control. By an axial displacement of the valve body while maintaining its rotary position it is possible to cancel the controlling action of the cooperating openings, i.e. of the outlet opening and the inlet opening, resulting in an increased pulse-like fluid supply to the mouthpiece connected to the grip member without the setting, i.e. the rotary position, of an actuating member comprising, for example, a rotatable as well as slidable adjustment ring being changed. In such a variant the activatable means for temporarily increasing the fluid supply to a mouthpiece are formed by the rotatable as well as slidable valve body and by the parts which cooperate with this valve body, such as a sealing cap and a reset spring.

We claim:

1. A dental cleaning device comprising a mouthpiece, and a grip member having (a) a fluid channel for supplying fluid to the mouthpiece (b) a fluid-flow control device which is adjustable by means of an actuating member which is movable between different actuating positions, and by means of which the amount of fluid supplied to the mouthpiece through the fluid channel during operation of the dental cleaning device is variable in accordance with the actuating positions of the actuating member, and (c) activatable means for temporarily increasing the amount of fluid supplied to the mouthpiece while the instantaneous actuating position of the actuating member for the fluid-flow control device is preserved.

2. A dental cleaning device comprising a mouthpiece and a grip member having a fluid channel for supplying fluid to the mouthpiece and having a fluid-flow control device which is adjustable by means of an actuating member, which is movable between different actuating positions, and by means of which the amount of fluid supplied to the mouthpiece through the fluid channel is variable in accordance with the actuating positions of the actuating member, wherein the grip member is provided with activatable means for temporarily increasing the amount of fluid supplied to the mouthpiece while the instantaneous actuating position of the actuating member for the fluid-flow control device is preserved, the activatable means comprising an additional fluid channel and a closing means which is switchable between a closed state and an open state to close and open the additional fluid channel.

3. A dental cleaning device as claimed in claim 2, wherein said actuating member is operable by hand and movable from a rest position into an operating position in order to actuate the closing means, and wherein the closing means occupies its open position and opens the additional fluid channel when the actuating member is in its operating position.

4. A dental cleaning device as claimed in claim 3, wherein the closing means is formed by a conical valve having an axially movable valve body which is loaded by a pressure spring, which urges the valve body in a direction from an open position corresponding to the open state of the closing means towards a closed position corresponding to the closed state of the closing means.

5. A dental cleaning device as claimed in claim 4 wherein the actuating member is arranged on a slide which is guided so as to be movable in the longitudinal direction of the grip member and which is slidable between an off-position and an on-position, and wherein with the slide in its off-position the closing means cannot be switched over by the actuating member and with the slide in its on-position the closing means can be switched over from its closed state to its open state by the actuating member.

6. A dental cleaning device as claimed in claim 3 wherein the actuating member is arranged on a slide which is guided so as to be movable in the longitudinal direction of the grip member and which is slidable between an off-position and an on-position, and wherein with the slide in its off-position the closing means cannot be switched over by the actuating member and with the slide in its on-position the closing means can be switched over from its closed state to its open state by the actuating member.

7. A dental cleaning device as claimed in claim 6, wherein actuating member includes a push-button subjected to the load of a pressure spring, which acts upon the slide and which urges the push-button in a direction from the operating position towards the rest position of the actuating member.

8. A dental cleaning device as claimed in claim 7, wherein the push-button is included in a slide knob which is guided so as to be movable in the longitudinal direction of the grip member and which traverses the slide knob with its part which points away from the grip member.

9. A dental cleaning device as claimed in claim 7 wherein the slide comprises an actuating portion and the fluid channel includes a further closing means which is movable between a closed state and an open state to close and open the fluid channel, which further closing means is switchable by means of the actuating portion of the slide, and is in its closed state when the slide is in its off-position and is in its open state when the slide is in its on-position.

10. A dental cleaning device as claimed in claim 6 wherein the slide comprises an actuating portion and the fluid channel includes a further closing means which is movable between a closed state and an open state to close and open the fluid channel, which further closing means is switchable by means of the actuating portion of the slide, and wherein the further closing means is in its closed state when the slide is in its off-position and the further closing means is in its open state when the slide is in its on-position.

11. A dental cleaning device as claimed in claim 10, wherein the further closing means is formed by a further conical valve having an axially movable valve body which is loaded by a pressure spring, which urges the valve body in a direction from an open position corresponding to the open state of the further closing means towards a closed position corresponding to the closed state of the further closing means.

12. A dental cleaning device as claimed claim 11, wherein the push-button is included in a slide knob which is guided so as to be movable in the longitudinal direction of the grip member and which traverses the slide knob with its part which points away from the grip member.

13. A dental cleaning device as claimed claim 10, wherein the push-button is included in a slide knob which is guided so as to be movable in the longitudinal direction of the grip member and which traverses the slide knob with its part which points away from the grip member.

14. A dental cleaning device comprising a mouthpiece and a grip member having a fluid channel for supplying fluid to the mouthpiece and having a fluid-flow control device provided on the grip member which is adjustable by means of an actuating member which is movable between different actuating positions, and by means of which the amount of fluid supplied to the mouthpiece through the fluid channel during operation of the dental cleaning device is variable in accordance with the actuating positions of the actuating member, and wherein the grip member is provided with activatable means for temporarily increasing the amount of fluid supplied to the mouthpiece while the setting of the actuating member for the fluid control-device at the time of activation of the activatable means is preserved.

* * * * *